(12) United States Patent
Yamashita et al.

(10) Patent No.: US 8,152,729 B2
(45) Date of Patent: Apr. 10, 2012

(54) TWO-DIMENSIONAL ARRAY ULTRASONIC PROBE

(75) Inventors: Yohachi Yamashita, Kanagawa-ken (JP); Noriko Yamamoto, Kanagawa-ken (JP); Kazuhiro Itsumi, Tokyo (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 581 days.

(21) Appl. No.: 12/347,045

(22) Filed: Dec. 31, 2008

(65) Prior Publication Data

US 2009/0209864 A1 Aug. 20, 2009

(30) Foreign Application Priority Data

Feb. 18, 2008 (JP) ................. 2008-035829

(51) Int. Cl.
*A61B 8/14* (2006.01)
*A61K 6/083* (2006.01)
(52) U.S. Cl. ........................ 600/459; 523/105
(58) Field of Classification Search ................ 600/459; 426/573; 525/192; 523/124, 105
See application file for complete search history.

(56) References Cited

U.S. PATENT DOCUMENTS

| | | | |
|---|---|---|---|
| 4,722,346 A * | 2/1988 | Chen | 600/459 |
| 5,834,687 A | 11/1998 | Talbot et al. | |
| 5,993,972 A * | 11/1999 | Reich et al. | 428/423.1 |
| 7,135,809 B2 | 11/2006 | Ossmann | |
| 7,307,374 B2 * | 12/2007 | Ossmann | 310/335 |
| 2003/0167556 A1 * | 9/2003 | Kelley | 2/206 |
| 2004/0122396 A1 * | 6/2004 | Maldonado et al. | 604/383 |
| 2006/0199884 A1 * | 9/2006 | Hoenig et al. | 524/230 |

FOREIGN PATENT DOCUMENTS

JP 3251328 11/2001

OTHER PUBLICATIONS

Fujii, Hideji. "Acoustic Properties of Lens Materials for Ultrasonic Probes." Jpn. J. Appl. Phys. vol. 34 (1995) pp. 312-315. Part 1, No. 1 Jan. 1995.*

* cited by examiner

*Primary Examiner* — Long V. Le
*Assistant Examiner* — Helene Bor
(74) *Attorney, Agent, or Firm* — Oblon, Spivak, McClelland, Maier & Neustadt, L.L.P.

(57) ABSTRACT

A two-dimensional array ultrasonic probe is provided with a two-dimensional ultrasonic array and a surface protection layer provided on the array. The two-dimensional ultrasonic array arranges a plurality of piezoelectric vibration elements two-dimensionally. The surface protection layer is made essentially of polybutadiene series rubber. The polybutadiene series rubber is synthesized from 100 parts by weight of polybutadiene and 1 to 5 parts by weight of glycerin.

5 Claims, 1 Drawing Sheet

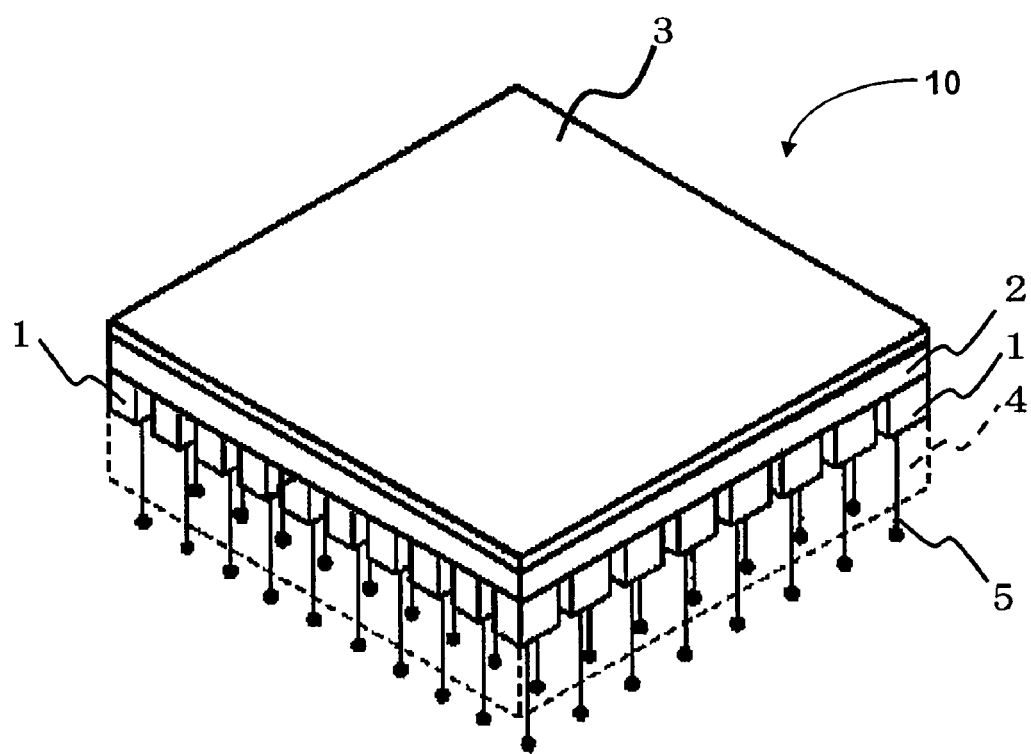

TWO-DIMENSIONAL ARRAY ULTRASONIC PROBE

CROSS REFERENCE TO RELATED APPLICATION

The application is based upon and claims the benefit of priority from the prior Japanese Patent Application No. 2008-035829, filed on Feb. 18, 2008, the entire contents of which are incorporated herein by reference.

FIELD OF THE INVENTION

The present invention relates to a two-dimensional ultrasonic probe, particularly relates to an ultrasonic probe suitable for medical use.

DESCRIPTION OF THE BACKGROUND

An ultrasonic probe is used for a fish finder, an ultrasonic diagnostic apparatus for a living body, etc. The ultrasonic probe is provided with a surface protection layer or an acoustic lens having acoustic protective functions when an ultrasonic beam is transmitted to a human body, etc.

Ultrasonic probes include a one-dimensional and two-dimensional array ultrasonic probe which arranges vibration elements one-dimensionally and two-dimensionally, respectively.

These days, a high-performance two-dimensional array probe capable of recognizing a volume of an object has been desired to be developed.

In a one-dimensional array ultrasonic probe with a one-dimensional array of vibration elements, a convex acoustic lens is formed in the outermost surface of the probe in order to focus ultrasonic waves transmitted from each vibration element. The lens is normally composed of rubber parts. Ultrasonic waves are focused basically in two directions of the one-dimensional probe. In a longitudinal direction, i.e., a direction along the one-dimensional array, focusing is done by delaying transmission timing of an ultrasonic wave from each element of the array. In a direction perpendicular to the longitudinal direction, focusing is done by using the convex acoustic lens. Acoustic impedance (AI=acoustic velocity× density) of the lens must be made closer to that of a human body (about 1.5 MRayls). However, it is advantageous to use materials for the lens having an acoustic velocity of 1000 m/s or less, which is lower than that of a human body, 1500 m/s, in order to obtain a feature of a convex lens. For this reason, materials having a rubber density of 1.5 g/cm³ or more and an acoustic velocity of 1000 m/s are used for the lens. On the other hand, ultrasonic waves transmitted from each vibration element can be focused electronically in a two-dimensional array ultrasonic probe with a two-dimensional array of vibration elements. Electronic focusing can be done in both X- and Y-directions of the array by delaying transmission timing of an ultrasonic wave from each vibration element. Therefore, it is not necessary to purposely provide materials of which acoustic velocity is lower than that of a human body for a surface layer of the array. It is essential to use materials of which acoustic velocity and density are as close as possible to those of a human body. For this reason, the surface layer is often called an "acoustic protection layer". The surface layer of the two-dimensional probe is different from that of the one-dimensional probe mentioned above from a viewpoint of the characteristics. Consequently, it is required to develop new materials for an acoustic protection layer of the two-dimensional probe.

There exists butadiene rubber as a material of which acoustic impedance is near to that of a human body. There has been an example where the material was used as an acoustic lens of a one-dimensional ultrasonic probe, published on JP-A 1996-615 (Kokai).

However, a surface protection layer used in a two-dimensional probe is thinner and flatter than an acoustic lens used in a one-dimensional probe. It is necessary to optimize mechanical strengths of butadiene series rubber to use it for the surface protection layer. It is further required to obtain good results to a biocompatibility test. Biocompatibility tests include a irritation test (irritation or intracutaneous reactivity), sentilization test, and cytotoxicity test.

SUMMARY OF THE INVENTION

An advantage of aspects of the invention is to provide a two-dimensional array ultrasonic probe provided with a surface protection layer having compatibility with a human body, a high mechanical strength and in particular low cytotoxicity.

To achieve the above advantage, an aspect of the invention is to provide a two-dimensional array ultrasonic probe which is provided with a two-dimensional ultrasonic array and a surface protection layer. The two-dimensional ultrasonic array arranges a plurality of piezoelectric vibration elements two-dimensionally. The surface protection layer is formed on a side of an ultrasonic transmission surface of the two-dimensional array ultrasonic probe, and contains polybutadiene series rubber. The polybutadiene series rubber is synthesized from 100 parts by weight of polybutadiene and 1 to 5 parts by weight of glycerin.

The surface protection layer may further contain inorganic particulates by 5 parts by weight or less.

The surface protection layer preferably has a Shore A hardness of 50 degrees or more at 37° C., a tear strength of 10 N/mm or more, a density of 0.96 g/cm³ to 1.04 g/cm³ and an acoustic velocity of 1450 m/s to 1600 m/s.

The polybutadiene series rubber may be hardened by a hardening agent containing isocyanate compounds.

The two-dimensional array ultrasonic probe of the invention is very compatible with a human body due to the low cytotoxicity

BRIEF DESCRIPTION OF THE DRAWING

FIG. 1 is a perspective view showing an outline of a two-dimensional array ultrasonic probe.

DETAILED DESCRIPTION OF THE INVENTION

An embodiment of the invention will be described below with reference to an accompanying drawing. The same reference numerals denote the same parts.

FIG. 1 is a perspective view showing an outline of a two-dimensional array ultrasonic probe 10. The two-dimensional probe 10 is provided with a two-dimensional ultrasonic array. Piezoelectric vibration elements 1 are arranged two-dimensionally in the probe 10. An acoustic matching layer 2 and a surface protection layer 3 are laminated one by one on an ultrasonic transmission surface of a two-dimensional ultrasonic array of the piezoelectric vibration elements 1. On the other hand, a backing element 4 is arranged in the back surface locating on the other side of the ultrasonic transmission surface of the array.

The piezoelectric vibration element 1 is provided with a piezoelectric object and a pair of electrodes formed on an ultrasonic transmission surface and a back surface of the piezoelectric object. The electrodes on the back surface are connected to a control means via an interconnection 5 running through the backing element 4. The electrodes on the ultrasonic transmission surface run through the acoustic matching layer 2, and are connected to the control means via an interconnection (not shown) formed between the acoustic matching layer 2 and the surface protecting layer 3.

An operation of the two-dimensional ultrasonic probe 10 with such a structure is explained. A voltage is applied between a pair of electrodes formed on each piezoelectric vibration element 1 to resonate it. This resonant action makes the element 1 transmit an ultrasonic wave from its ultrasonic transmission/reception surface. At the time of receiving, the piezoelectric vibration element vibrates according to an ultrasonic wave received by the ultrasonic transmission/reception surface, and this vibration is transduced into an electric signal. In the ultrasonic probe 10, the ultrasonic wave can be focused electronically in all the directions due to the two-dimensional array of the piezoelectric vibration elements 1.

The piezoelectric object used for the piezoelectric vibration elements 1 is a normal piezoelectric material comprising binary or ternary system ceramics. The piezoelectric objects are arrayed in a two-dimensional matrix. When using the piezoelectric vibration elements 1 as a two-dimensional ultrasonic probe for medical use, each piezoelectric vibration element measures 0.01 $mm^2$ to 0.2 $mm^2$ electrode-areal by 0.2 mm to 0.6 mm thick. The piezoelectric vibration elements 1 of this size are arrayed to form a 10×10 to 100×100 two-dimensional array. When the electrode area of the piezoelectric vibration elements 1 is larger than 0.2 $mm^2$, or when the two-dimensional array is formed of over 100×100 piezoelectric vibration elements 1, the ultrasonic transmission surface of the array becomes too large. The two-dimensional ultrasonic probe 10 with such a larger ultrasonic transmission surface will not be suitable for a probe for circulatory organs. It is because the probe for circulatory organs performs a medical examination of a human body particularly through the clearance between the two adjacent ribs. On the other hand, it is difficult to make the electrode area of each vibration element smaller than 0.01 $mm^2$ in respect of machining accuracy. Thicknesses of the piezoelectric vibration elements 1 are determined from kinds of vibration elements to use and wavelengths of ultrasonic waves to transmit. The two-dimensional array formed of less than 10×10 piezoelectric vibration elements 1 could be prevented from performing highly precise diagnosis.

The acoustic matching layer 2 performs acoustic impedance matching between a living body and the piezoelectric vibration elements 1. Materials with acoustic impedance which is intermediate between acoustic impedance of a living body and acoustic impedance of the piezoelectric vibration elements 1 will be used for the acoustic matching layer 2. Two or more layers comprising different materials may be laminated to provide an acoustic matching layer, matching acoustic impedance.

The backing element 4 is provided on the back surface of the piezoelectric vibration elements 1. The backing element 4 attenuates ultrasonic waves emitted from the back surface of the piezoelectric vibration elements 1 while supporting the piezoelectric vibration elements 1 mechanically. In order to fully attenuate ultrasonic waves, it is preferable to use the backing element 4 sufficiently thick with respect to wavelengths of the ultrasonic waves to be used.

The surface protection layer 3 is explained.

The surface protection layer 3 preferably meets the following 6 conditions.

(1) It is desirable that the surface protection layer 3 minimizes reflections of an ultrasonic wave from a living body. For this reason, the surface protection layer is required to be made from materials whose acoustic impedance (AI=acoustic velocity×density) is near acoustic impedance of a living body's skin. The acoustic impedance of a living body's skin is 1.53 MRayls at 37° C. The surface protection layer 3 for the two-dimensional ultrasonic probe 10 is required to have mostly the same acoustic velocity and the same density as those of a living body. The acoustic velocity and the density of a living body are about 1530 m/s and 0.96 $g/cm^3$ to 1.04 $g/cm^3$, respectively.

(2) The surface protection layer 3 is a path for an ultrasonic wave to be transmitted towards a human body from the ultrasonic vibration elements 1, and becomes a path for the ultrasonic vibration elements 1 to receive the ultrasonic wave reflected by the body. In order for the ultrasonic vibration elements 1 to transmit/receive an ultrasonic wave with high sensitivity, the surface protection layer 3 is required to be made from materials with a low attenuation coefficient at operating frequencies. The attenuation coefficient is desired to be less than 5 dB/cm/MHz, or to be less than 4 dB/cm/MHz preferably, e.g., at a frequency of 5 MHz and at 37° C.

(3) When using the two-dimensional ultrasonic probe 10, the surface protection layer 3 is pressed onto a living body at a considerably high pressure. The surface protection layer 3 normally comprises rubber. A shortage of the rubber hardness leads to a deformation of the surface protection layer, lowering image quality due to shifts of focal points for ultrasonic waves. This requires that a Shore A hardness of the material of the surface protection layer 3 for the two-dimensional array is to be 50 or more, or preferably 60 or more in the Shore A scale at 37° C. The Shore A hardness is evaluated with a durometer.

(4) The surface protection layer 3 is desired to have high formability, and to be particularly made from materials with high tear strengths. The acoustic protection layer 3 for the two-dimensional ultrasonic probe 10 whose main operation frequency is about 2 MHz to 5 MHz usually has a thickness of about 0.5 mm to 1.0 mm to be used. Hence, the acoustic protection layer 3 with a low tear strength often causes a breakdown of the two-dimensional ultrasonic probe 10, and also creates a risk that an electric current flows into a human body through the layer. On the other hand, materials with as low acoustic impedance as that of a human body generally tend to have a low tear strength. For this reason, materials with tear strength of 10 N/mm or more are desired to be developed.

(5) The surface protection layer 3, including additives contained in the layer, is required to be safe for a living body. Biocompatibility must be tested to check the safeties. Biocompatibility tests include an irritation test, intracutaneous reactivity test, sentilization test, cytotoxicity test, etc.

(6) Materials for the surface protection layer 3 are required to have little degradation by heat or light, i.e., to be chemically stable to acoustic coupling gel, antiseptic, etc. Glycerin water solution, ethyl alcohol, ethylene gas, etc. are one of those generally used as an acoustic coupling gel or an antiseptic. The materials need to maintain a high insulation resistance even under humid environment from a viewpoint of safety to a human body.

Butadiene rubber having acoustic impedance close to that of a human body has attracted attention, and its characteristics have been investigated. As a result, it has become clear that mechanical strength of butadiene rubber is not enough to use for a two-dimensional ultrasonic probe. Trials have been conducted to improve the mechanical strength by distributing inorganic particles in butadiene rubber. The strength of butadiene rubber increases as an additive amount of inorganic particles is made to increase, but it has turned out that a lot of inorganic particles are needed in order to obtain sufficient strength, and then the acoustic impedance of the butadiene rubber becomes extremely high compared with that of a human body as a result.

Use of liquid polybutadiene, as shown, e.g., by a chemical formula (1), enables us to synthesize polybutadiene series rubber using hardening agents such as diphenylmethane diisocyanate (MDI), as shown by a chemical formula (2), if necessary. A part of chemical formula for the polybutadiene series rubber obtained at this time is shown in a chemical formula (3).

[Formula 1]

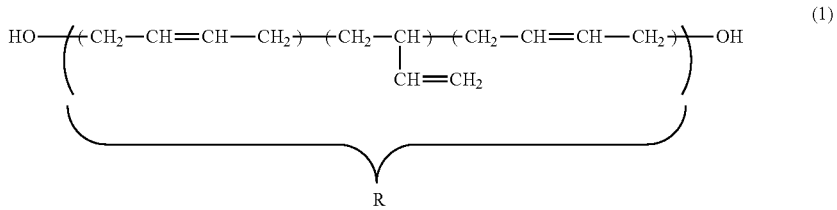

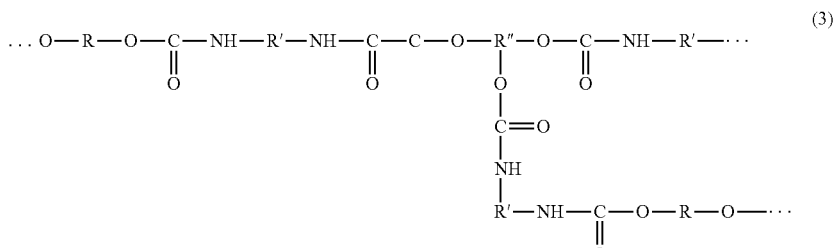

It has been found out by the present inventors that the polybutadiene series rubber which is formed by reacting glycerin with polybutadiene has acoustic impedance changing only slightly compared with the butadiene rubber made by the addition of the particles. It has been also found out that the polybutadiene series rubber also has both high mechanical strengths and biocompatibility.

The surface protection layer 3 according to the embodiment will be explained in detail below.

The surface protection layer 3 of the embodiment is the polybutadiene series rubber synthesized from 100 parts by weight of polybutadiene and 1 to 5 parts by weight of glycerin.

Reducing the amount of glycerin added to polybutadiene down to less 1 part by weight leads to a reduction in hardness of the surface protection layer 3 having the composition, the layer 3 having a Shore A hardness of 50 or less. Furthermore, the tear strength of the layer 3 goes down to 10 N/mm or less. It is, therefore, preferable to make the amount of glycerin into 1 or more parts by weight and furthermore 2 parts by weight or more in order to raise the mechanical strength. If the amount of glycerin exceeds 5 parts by weight, the acoustic impedance will go up to 1.65 MRayls or more. The attenuation coefficient also becomes high, going up to 5 dB/cm/MHz or more. The above mentioned results suggest that it is preferable to make the amount of glycerin 5 parts by weight or less and furthermore 4 parts by weight or less in order to raise the transmission/reception efficiency for ultrasonic waves.

The Shore A hardness, density, etc. of the polybutadiene series rubber thus obtained can be adjusted in accordance with the molecular weight of liquid polybutadiene, or the additive amount of the hardening agent. It is preferable to adjust the number average molecular weight of liquid polybutadiene and the amount of a hardening agent with respect to a total amount of polybutadiene and glycerin to about 2000 to 4000 and about 20 wt % to 40 wt %, respectively, e.g., in order to obtain a polybutadiene series rubber with a Shore A hardness of 50, density of 0.96 to 1.04 and an acoustic velocity of 1450 to 1600 m/s at 37° C.

It is possible to heighten moldability and mechanical strengths of the surface protection layer 3 by distributing inorganic particulates in polybutadiene series rubber. The attenuation coefficient of the surface protection layer 3 will increase, or the acoustic impedance of the layer 3 will become too high, as the additive amount of inorganic particulates increases. The above-mentioned results yield a preferable content of 0.1 to 5 parts by weight of inorganic particulates added to the polybutadiene series rubber. It is also preferable to use inorganic particulates with an average particle-diameter of 5 nm to 100 nm, furthermore 5 nm to 30 nm, in order to improve dispersibility of the inorganic particulates in the butadiene series rubber or to suppress an increase in the attenuation coefficient of the surface protection layer 3. The measurement of specific surface ($m^2/g$) of particulates provides an average particle-diameter of the particulates by calculations, assuming that a shape of the particulates is spherical. The specific materials of the inorganic particulates include silicon dioxide, titanium oxide, alumina, zinc oxide, zirconium dioxide, cerium oxide, ytterbium oxide, iron oxide, and carbon.

Inorganic particulates can be used with their surfaces coated by organic resin. As the organic resin, silicone resin such as cyclomethicone and dimethicone can be commonly used. After immersing inorganic particulates in a silicone resin bath and then taking them out of the bath, drying the particulates gives rise to a powder of silicone resin-coated inorganic particulates. The silicone resin-covered inorganic particulates can be kneaded into butadiene rubber. The dispersibility of the kneaded particulates can be improved to suppress an increase in the attenuation coefficient of the surface protection layer 3, and further to improve the moldability and strength of the layer 3. What is necessary is just to adjust the coating amount of the silicone resin to 1 wt % to 10 wt % with respect to the inorganic particulates.

The surface protection layer 3 also contains vulcanizing agents. The vulcanizing agents include, e.g., hexamethylene di-isocyanate, 2,2,4-trimethyl hexamethylene di-isocyanate, fatty series polyisocyanates such as lysinemethylester diisocyanate, hydrogenerated diphenylmethane diisocyanate, isophorone diisocyanate, alicyclic polyisocyanates, such as hydrogenerated tolylene diisocyanate, tolylene diisocyanate (TDI), diphenylmethane diisocyanate (MDI), naphthylene diisocyanate, xylylene diisocyanate, triphenylmethane triisocyanate, aromatic series polyisocyanates such as tris (4-phenyl isocyanate) thiophosphate, and composites made from one or more of these agents.

The surface protection layer 3 may also contain other various additive agents. For example, various characteristics of the surface protection layer 3 mentioned above are not spoiled greatly only when the amount of additive agents such as organic filler and color pigments is less than 1 wt %.

EXAMPLE

The present invention will be explained more specifically with reference to examples and comparative examples.

Examples 1 to 8 and Comparative Examples 1 to 5

Polybutadiene series rubbers according to examples 1 to 8 and comparative examples 1 to 5 were prepared. Liquid polybutadiene (made by Idemitsu petrochemical company, Poly bd R-45HT, 80% of 1,4-unsaturation and 20% of 1,2-unsaturation, molecular weight 2800), glycerin and diphenylmethane diisocyanate (MDI) as a hardening agent were provided. These substances were blended according to the recipes listed in Table 1. Each ratio expressed in parts by weight shown in Table 1 is the parts by weight of glycerin, MDI and other additives with respect to 100 parts by weight of polybutadiene.

The mixtures obtained were heated at 50° C. for 24 hours in a fluorine-treated container, and were further cured at room temperature for 100 hours to synthesize materials for the surface protection layer 3. After that, the mixtures were taken out of the container.

The materials blended for the surface protection layer 3 were processed into test samples with various shapes to evaluate the following characteristics of the samples by methods described below.

1) Density

Each material for the surface protection layer was processed into a 30 mm×30 mm×1 mm sample. The samples obtained were weighed in the air at 25° C. and in water, and then the density was calculated using the weights by an Archimedes method.

2) Acoustic Velocity and Attenuation Coefficient

Each material for the surface protection layer 3 was processed into a 30 mm×30 mm×1 mm sample.

The acoustic velocity was derived by the following procedure. The sample was sustained in water held at 37° C. to transmit a pulsed ultrasonic wave to the sample from a 5-MHz ultrasonic probe. A waveform having penetrated though the sample was measured using another 5-MHz ultrasonic probe. A pulsed ultrasonic wave was transmitted once again in the same water without the sample, and the penetration wave form was measured in the same way for calibration.

The acoustic velocity was derived from the sample thickness and a time difference between the two penetration wave forms measured in the water with and without the sample. The acoustic velocity (C) was calculated according to the following formula.

$$C=C_0/[1-C_0(\Delta t/d)]$$

$C_0$ and "d" represent the acoustic velocity for the water and the sample thickness, respectively. $\Delta t$ represents the time difference between two cross-points at which first peaks of the two penetration waveforms for the water only and the sample in the water firstly cross a time axis at the same sides of the peaks shoulders.

The attenuation coefficient was measured at 37° C. The sample thicknesses and an intensity difference between the two penetration wave forms measured in the water with and without the sample were used to derive the attenuation coefficients in a routine way.

3) Acoustic Impedance (AI)

AI was calculated as a product of the density and acoustic velocity measured at 37° C.

4) Hardness

The materials for surface protection layers 3 were processed into samples which measured 50 mm diametrical by 10 mm thick. The Shore A hardness of the samples obtained was measured at 37° C. using a durometer.

5) Tear Strength.

The materials for surface protection layers 3 were processed into crescent shape test specimen with a dimension of 110 mm×25 mm×2 mm according to JIS6252, and measured at n=5 using an INSTRON testing machine. The test provided tear strengths of the materials in a routine way.

6) Cytotoxicity

Cytotoxicity was tested in the following way.

Each material was cut finely into pieces of about 2 mm×15 mm. About 2.5 g-pieces were weighed and EOG-sterilized (40° C., 6 hours) for each material. The pieces were put into a fresh M05 culture medium so that a rate of 0.1 g/mL was made for each material to be tested. The culture medium containing the pieces was left at rest in a $CO_2$ incubator (5% $CO_2$, 37° C.) for 24 hours, providing a 100%-extraction undiluted solution of each material to be tested.

Soon after obtaining the 100%-extraction undiluted solution, the solution was diluted with an M05 fresh culture medium. Liquid samples with various concentrations (20, 40, 50, 60, 80, and 100%) were thus prepared. Each 2 mL of the liquid samples was provided.

V79 cells were cultivated in a $CO_2$ incubator (5% $CO_2$, 37° C.) using an Eagle's MEM medium (M05 medium) containing a fetal bovine blood serum (5 vol %) and sodium pyruvate (1 mmol/L).

The V79 cells cultivated were used to provide a suspension with a V79-cell concentration of $10^3$ cells/mL after being isolated using 0.25%-trypsin, and 0.1 mL of the suspension (100 cells) was dispensed into 6-wellplates with 2 mL of a culture medium in each well. After 24 hours passed, the culture medium was removed from each well of the 6-wellplates so that 100 cells adhered mostly 100% on a wall of each well of the 6-wellplates. Then 2 ml of the liquid samples with each concentration and a fresh M05 medium were poured to the wells of the 6-wellplates. That is, the culture mediums in the wells were replaced with 2 ml of the liquid samples and a fresh M05 medium. After the replacement, the 6-wellplates were incubated for 6 days. The fresh M05 medium was used for a negative contrast.

Removing the culture mediums after the 6-day cultivation, the cultivation of the V79 cells in the wells was stopped with methanol. Then, the V79 cells were dyed with a 10 vol % Giemsa staining solution. Colonies of the cells per well were observed with eyes using a multipurpose high-speed image analyzing device (Model No.-CA-11, SYSTEM SCIENCE Inc.). Relative cloning efficiency (%) of the samples with each concentration was calculated in comparison with the negative contrast (100% of the fresh M05 culture medium), and $IC_{50}$ values were obtained.

The values measured are shown in Table 1.

Comparative Example 6

Silicone rubber was prepared according to the recipe of a comparative example 6 shown in Table 1, and its characteristics were measured in a similar way to the above-mentioned examples 1 to 8 and comparative examples 1 to 5. The values measured are written together in Table 1.

Reference Example 1

Material for surface protection layers was synthesized using ethylene glycol instead of glycerin by the weight ratio according to a reference example 1 shown in Table 1, and its characteristics were evaluated, in the same way as the examples 1 to 8 and comparative examples 1 to 5. These values measured are included together to Table 1.

TABLE 1

| | | LIQUID POLY-BUTADIENE parts by weight | GLYCERIN parts by weight | HARDENING AGENT (LIQUID MDI) parts by weight | ADDITIVE parts by weight | DENSITY g/cm³ | ACOUSTIC VELOCITY m/s |
|---|---|---|---|---|---|---|---|
| EXAMPLE | 1 | 100 | 1 | 25 | — | 0.96 | 1540 |
| | 2 | 100 | 2 | 25 | — | 0.97 | 1532 |
| | 3 | 100 | 3 | 25 | — | 0.98 | 1530 |
| | 4 | 100 | 3.5 | 25 | — | 0.98 | 1529 |
| | 5 | 100 | 4 | 25 | — | 0.985 | 1532 |
| | 6 | 100 | 5 | 25 | — | 0.99 | 1540 |
| | 7 | 100 | 3 | 25 | $SiO_2$ = 5 | 1.02 | 1525 |
| | 8 | 100 | 3 | 25 | $SiO_2$ = 1 | 0.99 | 1532 |
| COMPARATIVE EXAMPLE | 1 | 100 | — | 12.5 | — | 0.94 | 1590 |
| | 2 | 100 | 10 | 30 | — | 1.02 | 1625 |
| | 3 | 100 | — | 12.5 | $SiO_2$ = 10 | 1.03 | 1479 |
| | 4 | 100 | — | 12.5 | $SiO_2$ = 20 | 1.16 | 1464 |
| | 5 | 100 | — | 12.5 | $SiO_2$ = 30 | 1.29 | 1453 |
| | 6 | silicone | — | — | — | 1.5 | 1000 |
| REFERENCE EXAMPLE | 1 | 100 | ethylene glycol = 100 | 33 | — | 1.02 | 1545 |

| | | ACOUSTIC IMPEDANCE Mrayls | ATTENUATION RATE dB/cm/MHz | SHORE A HARDNESS degrees | TEAR STRENGTH N/mm | CYTOTOXICITY TEST INDEX $IC_{50}$ |
|---|---|---|---|---|---|---|
| EXAMPLE | 1 | 1.48 | 2.1 | 50 | 10.5 | <1.0 |
| | 2 | 1.49 | 2.6 | 55 | 13 | <1.0 |
| | 3 | 1.50 | 3.1 | 58 | 16 | <1.0 |
| | 4 | 1.50 | 3.5 | 60 | 18 | <1.0 |
| | 5 | 1.51 | 3.9 | 61 | 21 | <1.0 |
| | 6 | 1.52 | 4.8 | 63 | 22 | <1.0 |
| | 7 | 1.56 | 3.7 | 65 | 22 | <1.0 |
| | 8 | 1.52 | 3.1 | 58 | 19 | <1.0 |
| COMPARATIVE EXAMPLE | 1 | 1.49 | 1.8 | 42 | 8 | <1.0 |
| | 2 | 1.66 | 7.2 | 72 | 22 | <1.0 |
| | 3 | 1.52 | 5.2 | 45 | 9 | <1.0 |
| | 4 | 1.70 | 5.9 | 48 | 14 | <1.0 |
| | 5 | 1.87 | 7 | 52 | 15 | <1.0 |
| | 6 | 1.50 | 11 | 80 | 13 | <1.0 |
| REFERENCE EXAMPLE | 1 | 1.58 | 4.9 | 88 | 28 | 28 |

Remarks: Average diameter of $SiO_2$ is about 100 nm.

The materials according to the examples have acoustic velocities and densities similar to those of a human body, specifically the acoustic impedance ranging from 1.48 to 1.52 MRalys, the attenuation coefficient being as small as 4.8 dB/cm/MHz or less.

The materials have a high Shore A hardness of 50 degrees or more and a high tear strength of 10 N/mm or more, enabling us to make the surface protection layer 3 for the two-dimensional array ultrasonic probe 10 with excellent reliability.

On the contrary, the butadiene rubber of the comparative example 1 without glycerin has an appropriately low attenuation coefficient, but has an inappropriately low Shore A hardness and tear strength, being not suitable for the surface protection layer 3. The butadiene rubber of the comparative example 2 with 10 parts by weight of glycerin has a sufficient hardness and strength, but has not only an excessively high attenuation coefficient but also excessively high acoustic impedance far from that of a human body. When filler of silicon dioxide ($SiO_2$) used generally is added to increase hardness, $SiO_2$ must be added by 30 wt % or more to make a Shore A hardness of 50 degrees or more for the butadiene rubber. In this case, the rubber obtained tends to have acoustic impedance of as high as 1.87 MRayls or more, being unsuitable to be used in the present application. Since viscosity of liquid butadiene rubber also tends to increase due to the filler addition, workability of the liquid is inferior and the added $SiO_2$ powder often forms precipitates in the liquid, and thus homogeneity may be often spoiled in some cases.

In the example where glycerin was used as a hardening agent, the value $IC_{50}$ is one or less, and is equivalent to that of silicone rubber series materials. However, in the reference example 1 where ethylene glycol was used, the $IC_{50}$ had a value of 28, higher than that of the rest.

What is claimed is:

1. A two-dimensional array ultrasonic probe comprising a two-dimensional ultrasonic array and a surface protection layer, the two-dimensional ultrasonic array arranging a plurality of piezoelectric vibration elements two-dimensionally, the surface protection layer being provided on a side of an ultrasonic transmission surface of the two-dimensional array ultrasonic probe, having a tear strength of 10 N/mm or more, and including polybutadiene series rubber, the polybutadiene series rubber being synthesized from 100 parts by weight of polybutadiene and 1 to 5 parts by weight of glycerin.

2. The probe according to claim 1, wherein the surface protection layer further contains inorganic particulates by five or less parts by weight.

3. The probe according to claim 1, wherein the surface protection layer has a Shore A hardness of 50 degrees or more at 37° C., a density of 0.96 $g/cm^3$ to 1.04 $g/cm^3$ and an acoustic velocity of 1450 m/s to 1600 m/s.

4. The probe according to claim 1, wherein the polybutadiene series rubber is hardened by a hardening agent containing isocyanate compounds.

5. The probe according to claim 1, wherein the probe is configured for a human body.

* * * * *